US00PP35637P2

(12) United States Plant Patent
Stott

(10) Patent No.: US PP35,637 P2
(45) Date of Patent: Feb. 6, 2024

(54) ***PITTOSPORUM* PLANT NAMED 'KFPIPB20'**

(50) Latin Name: *Pittosporum crassifolium*
Varietal Denomination: KFPIPB20

(71) Applicant: Peter Arlen Stott, Auckland (NZ)

(72) Inventor: Peter Arlen Stott, Auckland (NZ)

( * ) Notice: Subject to any disclaimer, the term of this patent is extended or adjusted under 35 U.S.C. 154(b) by 0 days.

(21) Appl. No.: 18/214,033

(22) Filed: Jun. 26, 2023

(51) Int. Cl.
*A01H 5/00* (2018.01)
*A01H 6/00* (2018.01)

(52) U.S. Cl.
USPC ..... Plt./234
CPC ..... *A01H 6/00* (2018.05)

(58) Field of Classification Search
USPC ..... Plt./234
CPC ..... A01H 5/00
See application file for complete search history.

*Primary Examiner* — Kent L Bell
(74) *Attorney, Agent, or Firm* — Cassandra Bright

(57) ABSTRACT

A new and distinct *Pittosporum* cultivar named 'KFPIPB20' is disclosed, characterized by a dwarf plant with a spherical, dense growth habit. Plants have short internodes, small obovate foliage and abundant basal branching. Plants are suitable for gardens, container cultivation and hedging. The new variety is a *Pittosporum*, typically produced as an outdoor ornamental plant.

3 Drawing Sheets

Latin name of the genus and species: *Pittosporum crassifolium.*

Variety denomination: 'KFPIPB20'.

BACKGROUND OF THE INVENTION

The new cultivar is a product of chance discovery. The new variety was discovered as a naturally occurring whole plant mutation of an unpatented, unnamed variety of *Pittosporum crassifolium*. The selection was made at a commercial nursery during October of 2019 in Auckland, New Zealand.

Asexual reproduction of the new cultivar 'KFPIPB20' was first performed at a commercial nursery in Auckland, New Zealand by terminal vegetative cuttings in 2020. Subsequent asexual propagation has shown that the unique features of this cultivar are stable and reproduced true to type.

The following traits have been repeatedly observed and are determined to be the unique characteristics of 'KFPIPB20.' These characteristics in combination distinguish 'KFPIPB20' as a new and distinct *Pittosporum crassifolium* cultivar:

1. Dwarf plant.
2. Exhibits extensive basal branching.
3. Shorter internodes (shorter than plants of the species known to the Inventor).
4. Compact and dense growth habit.
5. Smaller leaf relative to many naturally occurring seedlings of *Pittosporum crassifolium* known to the Inventor.

PARENT COMPARISON

Plants of the new cultivar 'KFPIPB20' are similar to the parent in most horticultural characteristics. The new variety, however, differs in the following:

1. The new variety is an overall much smaller plant than the parent variety.

2. The new variety has a more dense growth habit with more basal branching than the parent variety.
3. The new variety has smaller foliage than the parent variety.
4. The new variety has shorter internodes than the parent variety.

COMMERCIAL COMPARISON

'KFPIPB20' can be compared to the commercial variety *Pittosporum crassifolum* 'Green Lustre', unpatented. Plants of 'Green Lustre' are similar to plants of 'KFPIPB20' in most horticultural characteristics, however, plants of 'KFPIPB20' differ in the following:

1. 'KFPIPB20' is naturally dwarf, growing to about 1.2 meters in height; 'Green Lustre' is tall growing to about 4 meters in height.
2. 'KFPIPB20' is spherical in plant shape; 'Green Lustre' is narrow and upright.
3. 'KFPIPB20' leaves are obovate; leaves of 'Green Lustre' are elliptic.
4. 'KFPIPB20' has shorter internodes and compact growth; 'Green Lustre' is more open.

BRIEF DESCRIPTION OF THE PHOTOGRAPHS

The accompanying drawings illustrate in full color a typical plant of 'KFPIPB20' grown outdoors in Auckland, New Zealand.

Figure 1:
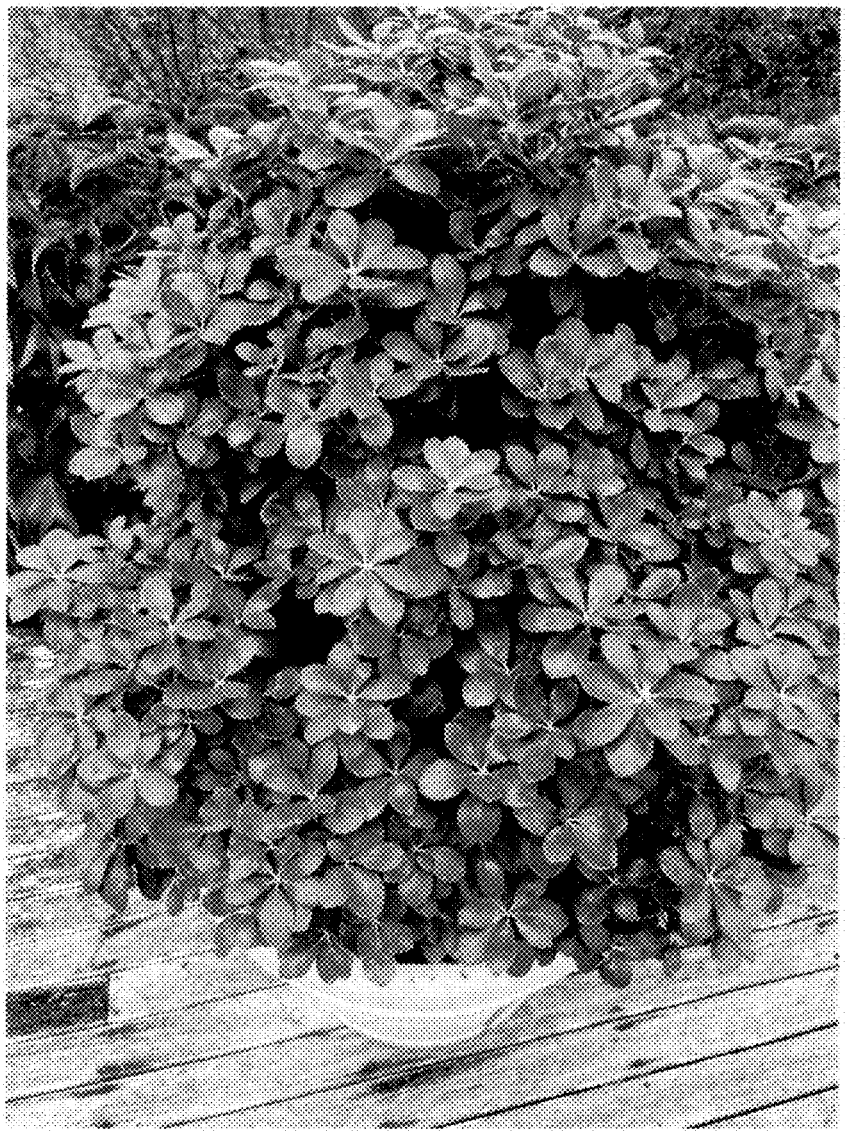
FIG. 1 illustrates a mature plant with foliage that has been somewhat shaded. This plant is approximately 30 months old, in a 2-gallon pot.
Figure 2:
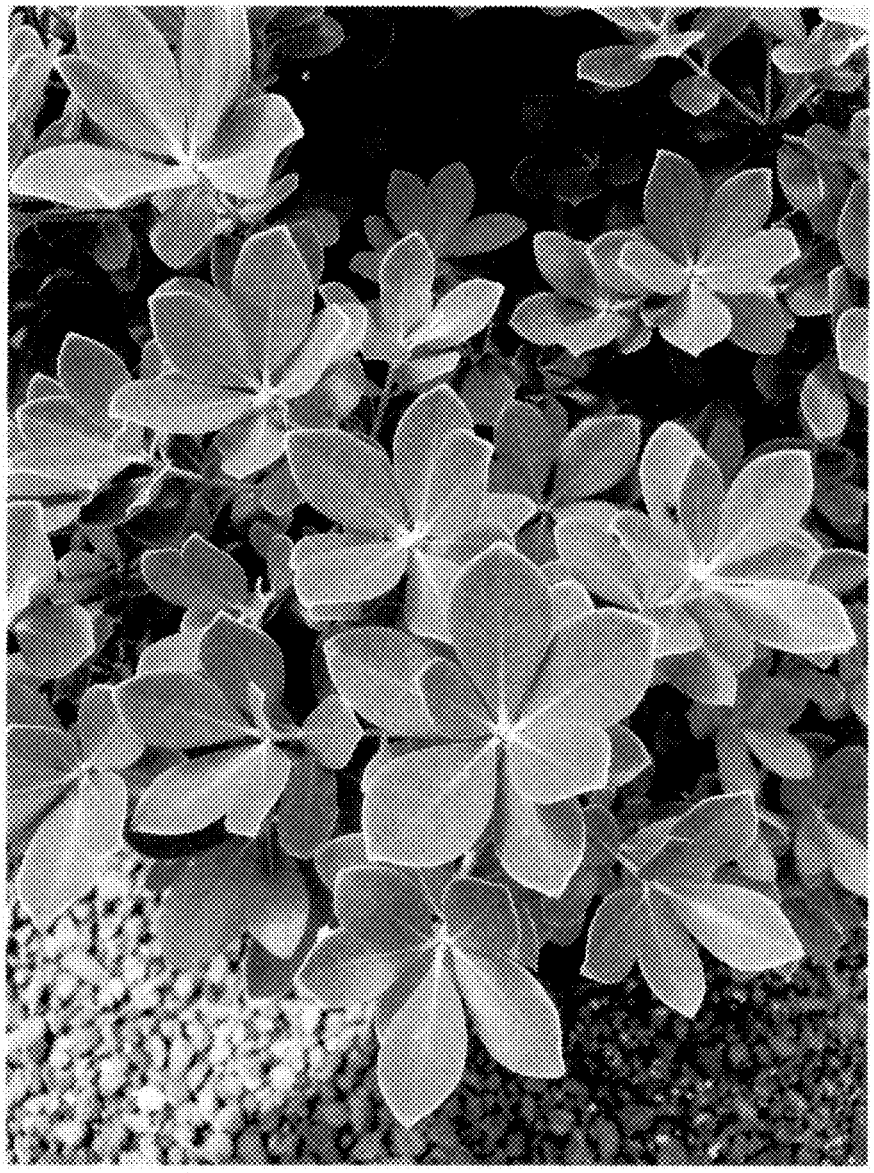
FIG. 2 illustrates spring foliage of the new variety.
Figure 3:
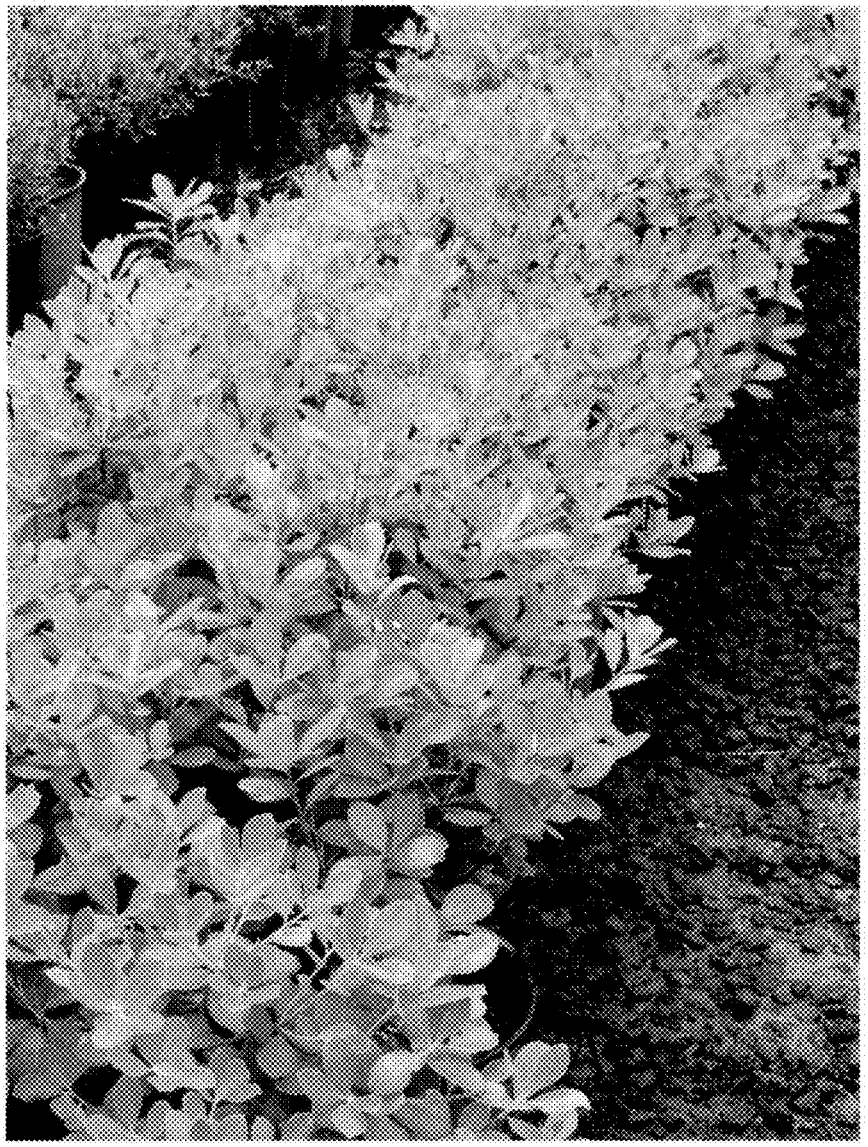
FIG. 3 illustrates multiple pots of the new variety during early spring, at approximately 12 months of age.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'KFPIPB20' plants grown outdoors in Dayton, OR. Temperatures ranged from about −2° C. to 8° C. at night to 5° C. to 28° C. during the day. No artificial light, photoperiodic treatments were given to the plants. Measurements and numerical values represent averages of typical plant types.

Botanical classification: *Pittosporum crassifolium* 'KFPIPB20'.

PROPAGATION

Type of propagation typically used: Semi-hardwood cuttings taken in late summer/early fall.

Time to produce a rooted cutting: 5 to 6 months to produce a 3-inch liner.

Root description: Very thin, dense, fibrous, not fleshy, freely branching. New roots colored near RHS Yellow-White 158D. Older roots colored near Grey-Brown 199D.

PLANT

Growth habit: Dense, evergreen, upright shrub.

Age of plant described: 18 months.

Container size: 3-gallon.

Overall plant shape: Spherical.

Growth habit: Freely branching with abundant basal branching.

Plant spread: 55 cm.

Plant height: 55 cm in second year.

Growth rate: Rapid.

Plant vigor: Good.

Branching description: Densely branched. About 10 to 12 primary branches near base of plant. Each primary branch has 3 to 4 main lateral branches. Main lateral branches densely branched with additional laterals. When pinched on average 3 new lateral branches emerge, occurring at acute angles, between 45° to 75°.

Primary branches:

*Length.*—Average range 30 to 50 cm, this varies based on pruning or pinching.

*Diameter.*—5 mm.

*Color.*—New growth: Near RHS Greyed-Green 193B. Old growth: Near RHS Grey-Brown 199C.

*Shape.*—Round.

*Strength.*—Moderate, somewhat flexible.

*Texture.*—New growth densely and softly pubescent. Mature growth lightly pubescent.

Internode length: Average range 1 to 2 cm.

Bark peel: Not observed.

FOLIAGE

Leaf:

*Arrangement.*—Alternate.

*Average length.*—4.1 to 5.2 cm.

*Average width.*—3.1 to 3.5 cm.

*Shape of blade.*—Obovate.

*Apex.*—Broad acute.

*Base.*—Broad attenuate.

*Margin.*—Entire.

*Aspect.*—Flat to slightly folded upward.

*Texture of top surface.*—Smooth.

*Texture of bottom surface.*—Smooth.

*Appearance of top surface.*—Moderately glossy.

*Appearance of bottom surface.*—Matte to slightly glossy.

*Color.*—Newest emerging foliage upper side: Near RHS Yellow-Green 145B. Newest emerging foliage under side: Near RHS Yellow-Green 145B flushed Greyed-Green 193B. Young foliage upper side: Near RHS Yellow-Green 145A. Young foliage under side: Near RHS Yellow-Green 145A flushed Greyed-Green 193B. Mature foliage upper side: Near RHS Green 137C. Mature foliage under side: Near RHS Green 138A. Venation: Type: Pinnate. Young foliage venation color upper side: Near RHS Yellow-Green 145C. Young foliage venation color under side: Near RHS Yellow-Green 145D. Mature foliage venation color upper side: Near RHS Yellow-Green 144C. Mature foliage venation color under side: Near RHS Yellow-Green 144D.

*Petiole.*—Length: 4 to 5 mm. Diameter: 2 mm. Color: Upper: Near Yellow-Green 145C. Lower: Near Yellow-Green 145D.

FLOWER

Not observed to date.

REPRODUCTIVE ORGANS

Not observed to date.

OTHER CHARACTERISTICS

Disease and pest resistance: Neither resistance nor susceptibility to normal diseases and pests of *Pittosporum* have been observed.

Drought tolerance and cold tolerance: Tolerates temperatures from approximately 0° C. to 40° C. Drought tolerance not tested to date.

Fruit/seed production: Not observed.

What is claimed is:

1. A new and distinct cultivar of *Pittosporum* plant named 'KFPIPB20' as herein illustrated and described.

* * * * *